US007959912B2

(12) United States Patent
Daube et al.

(10) Patent No.: US 7,959,912 B2
(45) Date of Patent: Jun. 14, 2011

(54) PROBIOTIC BIFIDOBACTERIAL SPECIES

(75) Inventors: Georges Daube, Stembert (BE); Veronique Delcenserie, Mississauga (CA); Françoise Gavini, Mons en Baroeul (FR)

(73) Assignee: Universite de Liege, Angleur (BE)

( * ) Notice: Subject to any disclaimer, the term of this patent is extended or adjusted under 35 U.S.C. 154(b) by 541 days.

(21) Appl. No.: 11/914,434

(22) PCT Filed: Mar. 31, 2006

(86) PCT No.: PCT/EP2006/061247
§ 371 (c)(1),
(2), (4) Date: Nov. 14, 2007

(87) PCT Pub. No.: WO2006/122850
PCT Pub. Date: Nov. 23, 2006

(65) Prior Publication Data
US 2008/0274085 A1    Nov. 6, 2008

(30) Foreign Application Priority Data

May 16, 2005   (EP) .................................... 05104071

(51) Int. Cl.
*A61K 35/74*   (2006.01)
*C12N 1/20*    (2006.01)
*A23C 9/127*   (2006.01)
(52) U.S. Cl. ......... 424/93.4; 435/252.1; 426/43; 426/61
(58) Field of Classification Search ............... 424/93.4; 435/252.1; 426/43, 61
See application file for complete search history.

(56) References Cited

FOREIGN PATENT DOCUMENTS

EP    1227152 A1 *   7/2002

OTHER PUBLICATIONS

Culligan et al. 2009. Probiotics and gastrointestinal disease: successes, problems and future prospects. Gut Pathogens, 1:19, p. 1-12.*
SCORE sequence search results. 2010. p. 1-33.*
Biavati et al. "Bifidobacteria: history, ecology, physiology and applications." *Annals of Microbiology*. 50: 117-131 (2004).
Dong et al. *Bifidobacterium thermacidophilum* sp. nov., isolated from an anaerobic digester. *Int. J. Syst. Evol. Microbiol.* 50: 119-125 (2000).
EBI database accession No. AY174108 (2003.).
Simpson et al. "*Bifidobacterium psychraerophilum* sp. nov. and *Aeriscardovia aeriphila* gen. nov., sp., isolated from a porcine caecum." *International Journal of Systematic Evolutionary Microbiology*. 54: 401-406 (2004).
Simpson et al. "Genomic diversity and relatedness of bifidobacteria isolated from porcine cecum." *Journal of Bacteriology*. 185(8): 2571-2581 (2003).

* cited by examiner

*Primary Examiner* — Taeyoon Kim
(74) *Attorney, Agent, or Firm* — Merchant & Gould P.C.; Brian R. Dorn

(57) ABSTRACT

A probiotic composition comprising a *Bifidobacterium* strain which has DNA sequence homology of greater than 40% to *Bifidobacterium* GC56, wherein *Bifidobacterium* GC56 was deposited at the Collection Nationale de Cultures de Microorganismes (CNCM, Institut Pasteur) on 9 Dec. 2004 with accession number CNCM 1-3342.

20 Claims, 8 Drawing Sheets

Figure 1:
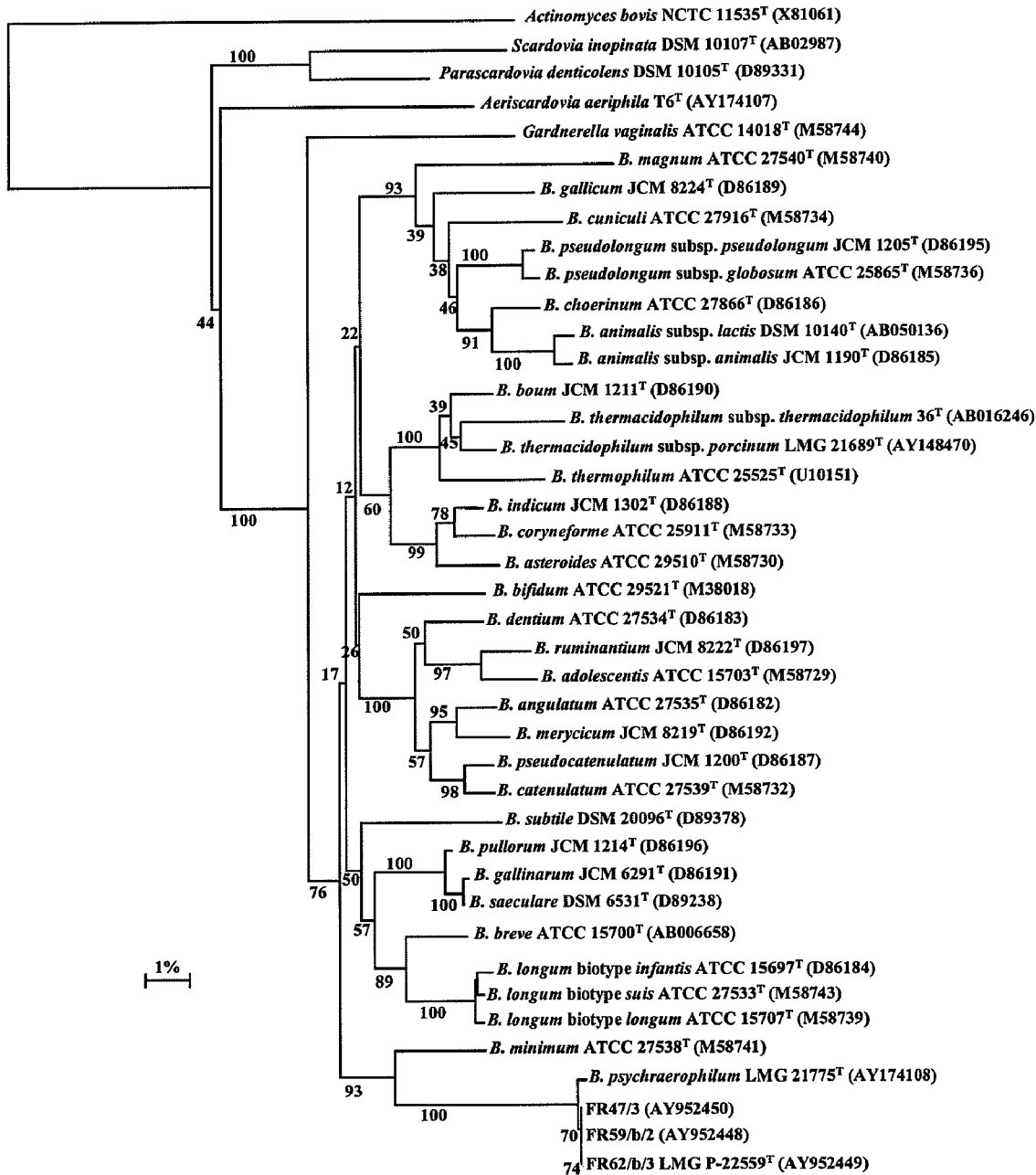

```
          10        20        30        40        50        60
1 GTCAGGATGAACGCTGGCGGCGTGCTTAACACATGCAAGTCGAACGGGATCCATCAAGCT   60
2 ------------------------------------GTCGAACGGGATCCATCAAGCT   22
3 ------------------------------------------------ATCCATCAAGCT   12
4 --------------------------------------------AGGGATCCATCAAGCT   16
C ........................................:::::::+++ATCCATCAAGCT
          70        80        90       100       110       120
1 TGCTTGATGGTGAGAGTGGCGAACGGGTGAGTAATACGTGACTAACCTGCCTCATACACC  120
2 TGCTTGATGGTGAGAGTGGCGAACGGGTGAGTAATGCGTGACTAACCTGCCTCATACACC   82
3 TGCTTGATGGTGAGAGTGGCGAACGGGTGAGTAATGCGTGACTAACCTGCCTCATACACC   72
4 TGCTTGATGGTGAGAGTGGCGAACGGGTGAGTAATGCGTGACTAACCTGCCTCATACACC   76
C TGCTTGATGGTGAGAGTGGCGAACGGGTGAGTAAT+CGTGACTAACCTGCCTCATACACC 130       140       150       160       170       180
1 GGAATAGCTCCTGGAAACGGGTGGTAATGCCGGATGCTCCAACATTTCACATGTTTTGTT  180
2 GGAATAGCTCCTGGAAACGGGTGGTAATGCCGGATGCTCCAACATTTCACATGTTTTGTT  142
3 GGAATAGCTCCTGGAAACGGGTGGTAATGCCGGATGCTCCAACATTTCACATGTTTTGTT  132
4 GGAATAGCTCCTGGAAACGGGTGGTAATGCCGGATGCTCCAACATTTCACATGTTTTGTT  136
C GGAATAGCTCCTGGAAACGGGTGGTAATGCCGGATGCTCCAACATTTCACATGTTTTGTT 190       200       210       220       230       240
1 GGGAAAGCGTTAGCGGTATGAGATGGGGTCGCGTCCTATCAGCTTGTTGGTGAGGTAATG  240
2 GGGAAAGCGTTAGCGGTATGAGATGGGGTCGCGTCCTATCAGCTTGTTGGTGAGGTAATG  202
3 GGGAAAGCGTTAGCGGTATGAGATGGGGTCGCGTCCTATCAGCTTGTTGGTGAGGTAATG  192
4 GGGAAAGCGTTAGCGGTATGAGATGGGGTCGCGTCCTATCAGCTTGTTGGTGAGGTAATG  196
C GGGAAAGCGTTAGCGGTATGAGATGGGGTCGCGTCCTATCAGCTTGTTGGTGAGGTAATG 250       260       270       280       290       300
1 GCTCACCAAGGCTTCGACGGGTAGCCGGCCTGAGAGGGCGACCGGCCACATTGGGACTGA  300
2 GCTCACCAAGGCTTCGACGGGTAGCCGGCCTGAGAGGGCGACCGGCCACATTGGGACTGA  262
3 GCTCACCAAGGCTTCGACGGGTAGCCGGCCTGAGAGGGCGACCGGCCACATTGGGACTGA  252
4 GCTCACCAAGGCTTCGACGGGTAGCCGGCCTGAGAGGGCGACCGGCCACATTGGGACTGA  256
C GCTCACCAAGGCTTCGACGGGTAGCCGGCCTGAGAGGGCGACCGGCCACATTGGGACTGA
```

Figure 2

```
             310        320        330        340        350        360
1 GATACGGCCCAGACTCCTACGGGAGGCAGCAGTGGGGAATATTGCACAATGGGCGAAAGC   360
2 GATACGGCCCAGACTCCTACGGGAGGCAGCAGTGGGGAATATTGCACAATGGGCGAAAGC   322
3 GATACGGCCCAGACTCCTACGGGAGGCAGCAGTGGGGAATATTGCACAATGGGCGAAAGC   312
4 GATACGGCCCAGACTCCTACGGGAGGCAGCAGTGGGGAATATTGCACAATGGGCGAAAGC   316
C GATACGGCCCAGACTCCTACGGGAGGCAGCAGTGGGGAATATTGCACAATGGGCGAAAGC 370        380        390        400        410        420
1 CTGATGCAGCGACGCCGCGTGCGGGATGAAGGCCTTCGGGTTGTAAACCGCTTTTAATTG   420
2 CTGATGCAGCGACGCCGCGTGCGGGATGAAGGCCTTCGGGTTGTAAACCGCTTTTAATTG   382
3 CTGATGCAGCGACGCCGCGTGCGGGATGAAGGCCTTCGGGTTGTAAACCGCTTTTAATTG   372
4 CTGATGCAGCGACGCCGCGTGCGGGATGAAGGCCTTCGGGTTGTAAACCGCTTTTAATTG   376
C CTGATGCAGCGACGCCGCGTGCGGGATGAAGGCCTTCGGGTTGTAAACCGCTTTTAATTG 430        440        450        460        470        480
1 GGAGCAAGCGAGAGTGAGTGTACCTTTTGAATAAGCACCGGCTAACTACGTGCCAGCAGC   480
2 GGAGCAAGCGAGAGTGAGTGTACCTTTTGAATAAGCACCGGCTAACTACGTGCCAGCAGC   442
3 GGAGCAAGCGAGAGTGAGTGTACCTTTTGAATAAGCACCGGCTAACTACGTGCCAGCAGC   432
4 GGAGCAAGCGAGAGTGAGTGTACCTTTTGAATAAGCACCGGCTAACTACGTGCCAGCAGC   436
C GGAGCAAGCGAGAGTGAGTGTACCTTTTGAATAAGCACCGGCTAACTACGTGCCAGCAGC 490        500        510        520        530        540
1 CGCGGTAATACGTAGGGTGCAAGCGTTATCCGGAATTATTGGGCGTAAAGAGCTCGTAGG   540
2 CGCGGTAATACGTAGGGTGCAAGCGTTATCCGGAATTATTGGGCGTAAAGAGCTCGTAGG   502
3 CGCGGTAATACGTAGGGTGCAAGCGTTATCCGGAATTATTGGGCGTAAAGAGCTCGTAGG   492
4 CGCGGTAATACGTAGGGTGCAAGCGTTATCCGGAATTATTGGGCGTAAAGAGCTCGTAGG   496
C CGCGGTAATACGTAGGGTGCAAGCGTTATCCGGAATTATTGGGCGTAAAGAGCTCGTAGG 550        560        570        580        590        600
1 CGGTTTGTCACGCCTGGTGTGAAAGTCCATCGCTTAACGGTGGATCTGCGCCGGGTACGG   600
2 CGGTTTGTCACGCCTGGTGTGAAAGTCCATCGCTTAACGGTGGATCTGCGCCGGGTACGG   562
3 CGGTTTGTCACGCCTGGTGTGAAAGTCCATCGCTTAACGGTGGATCTGCGCCGGGTACGG   552
4 CGGTTTGTCACGCCTGGTGTGAAAGTCCATCGCTTAACGGTGGATCTGCGCCGGGTACGG   556
C CGGTTTGTCACGCCTGGTGTGAAAGTCCATCGCTTAACGGTGGATCTGCGCCGGGTACGG
```

Figure 2 continued

```
              610        620        630        640        650        660
1 GCAGGCTAGAGTGCAGTAGGGGAGATTGGAATTCCCGGTGTAACGGTGGAATGTGTAGAT 660
2 GCAGGCTAGAGTGCAGTAGGGGAGATTGGAATTCCCGGTGTAACGGTGGAATGTGTAGAT 622
3 GCAGGCTAGAGTGCAGTAGGGGAGATTGGAATTCCCGGTGTAACGGTGGAATGTGTAGAT 612
4 GCAGGCTAGAGTGCAGTAGGGGAGATTGGAATTCCCGGTGTAACGGTGGAATGTGTAGAT 616
C GCAGGCTAGAGTGCAGTAGGGGAGATTGGAATTCCCGGTGTAACGGTGGAATGTGTAGAT 670        680        690        700        710        720
1 ATCGGGAAGAACACCAATGGCGAAGGCAGATCTCTGGGCTGTTACTGACGCTGAGGAGCG 720
2 ATCGGGAAGAACACCAATGGCGAAGGCAGATCTCTGGGCTGTTACTGACGCTGAGGAGCG 682
3 ATCGGGAAGAACACCAATGGCGAAGGCAGATCTCTGGGCTGTTACTGACGCTGAGGAGCG 672
4 ATCGGGAAGAACACCAATGGCGAAGGCAGATCTCTGGGCTGTTACTGACGCTGAGGAGCG 676
C ATCGGGAAGAACACCAATGGCGAAGGCAGATCTCTGGGCTGTTACTGACGCTGAGGAGCG 730        740        750        760        770        780
1 AAAGCATGGGGAGCGAACAGGATTAGATACCCTGGTAGTCCATGCCGTAAACGGTGGATG 780
2 AAAGCATGGGGAGCGAACAGGATTAGATACCCTGGTAGTCCATGCCGTAAACGGTGGATG 742
3 AAAGCATGGGGAGCGAACAGGATTAGATACCCTGGTAGTCCATGCCGTAAACGGTGGATG 732
4 AAAGCATGGGGAGCGAACAGGATTAGATACCCTGGTAGTCCATGCCGTAAACGGTGGATG 736
C AAAGCATGGGGAGCGAACAGGATTAGATACCCTGGTAGTCCATGCCGTAAACGGTGGATG 790        800        810        820        830        840
1 CTGGATGTGGGGCCCTTCCACGGGCTCCGTGTCGGAGCTAACGCGTTAAGCATCCCGCCT 840
2 CTGGATGTGGGACCCTTCCACGGGTTCCGTGTCGGAGCTAACGCGTTAAGCATCCCGCCT 802
3 CTGGATGTGGGACCCTTCCACGGGTTCCGTGTCGGAGCTAACGCGTTAAGCATCCCGCCT 792
4 CTGGATGTGGGACCCTTCCACGGGTTCCGTGTCGGAGCTAACGCGTTAAGCATCCCGCCT 796
C CTGGATGTGGG+CCCTTCCACGGG+TCCGTGTCGGAGCTAACGCGTTAAGCATCCCGCCT 850        860        870        880        890        900
1 GGGGAGTACGGCCGCAAGGCTAAAACTCAAAGAAATTGACGGGGGCCCGCACAAGCGGCG 900
2 GGGGAGTACGGCCGCAAGGCTAAAACTCAAAGAAATTGACGGGGGCCCGCACAAGCGGCG 862
3 GGGGAGTACGGCCGCAAGGCTAAAACTCAAAGAAATTGACGGGGGCCCGCACAAGCGGCG 852
4 GGGGAGTACGGCCGCAAGGCTAAAACTCAAAGAAATTGACGGGGGCCCGCACAAGCGGCG 856
C GGGGAGTACGGCCGCAAGGCTAAAACTCAAAGAAATTGACGGGGGCCCGCACAAGCGGCG
```

Figure 2 continued

```
            910        920        930        940        950        960
1 GAGCATGCGGATTAATTCGATGCAACGCGAAGAACCTTACCTAGGCTTGACATGTTTCGG  960
2 GAGCATGCGGATTAATTCGATGCAACGCGAAGAACCTTACCTAGGCTTGACATGTTTCGG  922
3 GAGCATGCGGATTAATTCGATGCAACGCGAAGAACCTTACCTAGGCTTGACATGTTTCGG  912
4 GAGCATGCGGATTAATTCGATGCAACGCGAAGAACCTTACCTAGGCTTGACATGTTTCGG  916
C GAGCATGCGGATTAATTCGATGCAACGCGAAGAACCTTACCTAGGCTTGACATGTTTCGG 970        980        990       1000       1010       1020
1 ACAGCCCCAGAGATGGGGTCTCCCTTCGGGGCCGATTCACAGGTGGTGCATGGTCGTCGT 1020
2 ACAGCCCCAGAGATGGGGTCTCCCTTCGGGGCCGATTCACAGGTGGTGCATGGTCGTCGT  982
3 ACAGCCCCAGAGATGGGGTCTCCCTTCGGGGCCGATTCACAGGTGGTGCATGGTCGTCGT  972
4 ACAGCCCCAGAGATGGGGTCTCCCTTCGGGGCCGATTCACAGGTGGTGCATGGTCGTCGT  976
C ACAGCCCCAGAGATGGGGTCTCCCTTCGGGGCCGATTCACAGGTGGTGCATGGTCGTCGT 1030       1040       1050       1060       1070       1080
1 CAGCTCGTGTCGTGAGATGTTGGGTTAAGTCCCGCAACGAGCGCAACCCTCGCCTTGTGT 1080
2 CAGCTCGTGTCGTGAGATGTTGGGTTAAGTCCCGCAACGAGCGCAACCCTCGCCTTGTGT 1042
3 CAGCTCGTGTCGTGAGATGTTGGGTTAAGTCCCGCAACGAGCGCAACCCTCGCCTTGTGT 1032
4 CAGCTCGTGTCGTGAGATGTTGGGTTAAGTCCCGCAACGAGCGCAACCCTCGCCTTGTGT 1036
C CAGCTCGTGTCGTGAGATGTTGGGTTAAGTCCCGCAACGAGCGCAACCCTCGCCTTGTGT 1090       1100       1110       1120       1130       1140
1 TGCCAGCACGTTATGGTGGGAACTCACAAGGGACCGCCGGGGTTAACTCGGAGGAAGGTG 1140
2 TGCCAGCACGTTATGGTGGGAACTCACAAGGGACCGCCGGGGTTAACTCGGAGGAAGGTG 1102
3 TGCCAGCACGTTATGGTGGGAACTCACAAGGGACCGCCGGGGTTAACTCGGAGGAAGGTG 1092
4 TGCCAGCACGTTATGGTGGGAACTCACAAGGGACCGCCGGGGTTAACTCGGAGGAAGGTG 1096
C TGCCAGCACGTTATGGTGGGAACTCACAAGGGACCGCCGGGGTTAACTCGGAGGAAGGTG 1150       1160       1170       1180       1190       1200
1 GGGATGACGTCAGATCATCATGCCCCTTACGTCTAGGGCTTCACGCATGCTACAATGGCC 1200
2 GGGATGACGTCAGATCATCATGCCCCTTACGTCTAGGGCTTCACGCATGCTACAATGGCC 1162
3 GGGATGACGTCAGATCATCATGCCCCTTACGTCTAGGGCTTCACGCATGCTACAATGGCC 1152
4 GGGATGACGTCAGATCATCATGCCCCTTACGTCTAGGGCTTCACGCATGCTACAATGGCC 1156
C GGGATGACGTCAGATCATCATGCCCCTTACGTCTAGGGCTTCACGCATGCTACAATGGCC
```

Figure 2 continued

```
         1210       1220       1230       1240       1250       1260
1 GGTACAACGAGATGCGACATGGCGACATGAAGCGAATCTCTTAAAACCGGTCTCAGTTCG 1260
2 GGTACAACGAGATGCGACATGGCGACATGAAGCGAATCTCTTAAAACCGGTCTCAGTTCG 1222
3 GGTACAACGAGATGCGACATGGCGACATGAAGCGAATCTCTTAAAACCGGTCTCAGTTCG 1212
4 GGTACAACGAGATGCGACATGGCGACATGAAGCGAATCTCTTAAAACCGGTCTCAGTTCG 1216
C GGTACAACGAGATGCGACATGGCGACATGAAGCGAATCTCTTAAAACCGGTCTCAGTTCG 1270       1280       1290       1300       1310       1320
1 GATTGGAGCCTGCAACTCGGCTCCATGAAGGCGGAGTCGCTAGTAATCGCGAATCAGCAA 1320
2 GATTGGAGCCTGCAACTCGGCTCCATGAAGGCGGAGTCGCTAGTAATCGCGAATCAGCAA 1282
3 GATTGGAGCCTGCAACTCGGCTCCATGAAGGCGGAGTCGCTAGTAATCGCGAATCAGCAA 1272
4 GATTGGAGCCTGCAACTCGGCTCCATGAAGGCGGAGTCGCTAGTAATCGCGAATCAGCAA 1276
C GATTGGAGCCTGCAACTCGGCTCCATGAAGGCGGAGTCGCTAGTAATCGCGAATCAGCAA
         1330       1340       1350       1360       1370       1380
1 CGTCGCGGTGAATGCGTTCCCGGGCCTTGTACACACCGCCCGTCAAGTCATGAAAGTGGG 1380
2 CGTCGCGGTGAATGCGTTCCCGGGCCTTGTACACACCGCCCGTCAAGTCATGAAAGTGGG 1342
3 CGTCGCGGTGAATGCGTTCCCGGGCCTTGTACACACCGCCCGTCAAGTCATGAAAGTGGG 1332
4 CGTCGCGGTGAATGCGTTCCCGGGCCTTGTACACACCGCCCGTCAAGTCATGAAAGTGGG 1336
C CGTCGCGGTGAATGCGTTCCCGGGCCTTGTACACACCGCCCGTCAAGTCATGAAAGTGGG 1390       1400       1410       1420
1 TAGCACCCGAAGCCGGTGGCCTAACCTTTTGGAGGGAGCCGTCTAAGG              1428
2 TAGCACCCGAAGCCGGTGGCCTAACCTTTT-----------------              1372
3 TAGCACCCGAAGCCGGTGGCCTAA-----------------------              1356
4 TAGCACCCGAAGCCGGTGGCCTAACCTTTTGGAGGGAGCCGTCTAAGG              1384
C TAGCACCCGAAGCCGGTGGCCTAA++++++:::::::::::::::::
```

Figure 2 continued

| Seq ID no | | | |
|---|---|---|---|
| AY004274 | CGTCACCGCCGGCTCCAACCCGATCGCTTTGCGTCGTGGTATCGAGAAGG | 112 | 7 |
| FR47/3 | CGTCGTTGCGGGCTCCAACCCCATCGCTCTTCGTCGCGGCATCGAGAAGG | 65 | 8 |
| FR54/e/1 | CGTCGTTGCGGGCTCCAACCCCATCGCTCTTCGTCGCGGCATCGAGAAGG | 70 | 9 |
| AF210319 | CGTCACCGCCGGTTCCAACCCGATCGCGCTGCGTCGTGGCATCGAGAAGG | 550 | 10 |
| AF240571 | CGTCACCGCCGGCTCCAACCCGATCGCGCTGCGTCGCGGCATCGAAAAGG | 112 | 11 |
| AY004277 | CGTGGTCGCCGGCTCCAACCCGATCGCTCTGCGTCGCGGTATCGAGAAGG | 112 | 12 |
| AF240568 | CGTGGTCGCCGGCTCCAACCCGATTGCGCTGCGCCGCGGCATTGAAAAGG | 113 | 13 |
| FR51/h/1 | ---CGTTTGTGGCNTTAGCC--ATCGCTCTTCGTCGCGGCATCGAGAAGG | 45 | 14 |
| FR59/b/2 | ----------------GCC--ATCGCTCTTCGTCGCGGCATCGAGAAGG | 31 | 15 |
| | *  ** **  * ** ** ** ** ** ** **** | | |
| AY004274 | CTTCCGAAGCCATCTCAAGGAGCTTATCGCAGCTGCCAAGGACGTTGAG | 162 | 16 |
| FR47/3 | CCTCAGACGCCATCGTCAAGGAGCTGATTTCCGCAGCCAAGGACGTTGAG | 115 | 17 |
| FR54/e/1 | CCTCAGACGCCATCGTCAAGGAGCTGATTTCCGCAGCCAAGGACGTTGAG | 120 | 18 |
| AF210319 | CCGCCGACGCCATCGTCAAGGAACTCGTCGCAGCGGCCAAGGACGTTGAG | 600 | 19 |
| AF240571 | CTTCCGACGCCATTGTCAAGGAACTTGTCGCGGCCGCCAAGGATGTCGAG | 162 | 20 |
| AY004277 | CCACCGAAGTCATCGTCAAGGAACTCGTCGCCGCCGCCAAGGACGTCGAG | 162 | 21 |
| AF240568 | CCGCCGACGCCATCGTCAAGGAACTCGTCGCAGCCGCCAAGGACGTCGAG | 163 | 22 |
| FR51/h/1 | C-TCAGACGCCATCGTCAAGGAGCTGATTTCCGCAGCCAAGGACGTTGAG | 94 | 23 |
| FR59/b/2 | CCTCAGACGCCATCGTCAAGGAGCTGATTTCCGCAGCCAAGGACGTTGAG | 81 | 24 |
| | *  *  ** *  *** ********  **    *   *  ** ******** **  *** | | |
| AY004274 | ACCAAGGATCAGATCGCCGCTACCGCAACGATTTCCGCCGCCGATCCGGA | 212 | 25 |
| FR47/3 | ACCAAGGATCAGATCGCCGCGACGGCAACGATCTCCGCGGCCGATCCCGA | 165 | 26 |
| FR54/e/1 | ACCAAGGATCAGATCGCCGCGACGGCAACGATCTCCGCGGCCGATCCCGA | 170 | 27 |
| AF210319 | ACCAAGGATCAGATCGCTGCCACCGCAACGATTTCCGCCGCTGATCCGGA | 650 | 28 |
| AF240571 | ACCAAGGACCAGATCGCTGCCACCGCAACGATCTCCGCCGCTGATCCGGA | 212 | 29 |
| AY004277 | ACCAAGGATCAGATCGCTGCCACTGCTACGATCTCCGCCGCCGATCCTGA | 212 | 30 |
| AF240568 | ACCAAGGATCAGATCGCTGCCACCGCAACGATTTCCGCCGCCGATCCCGA | 213 | 31 |
| FR51/h/1 | ACCAAGGATCAGATCGCCGCGACGGCAACGATCTCCGCGGCCGATCCCGA | 144 | 32 |
| FR59/b/2 | ACCAAGGATCAGATCGCCGCGACGGCAACGATCTCCGCGGCCGATCCCGA | 131 | 33 |
| | ******** ******** ** **  ** ***** ***** ** ***** ** | | |
| AY004274 | AGTCGGCGAGAAGATCGCCGAAGCTCTTGACAAGGTTGGCCAGGACGGCG | 262 | 34 |
| FR47/3 | GGTTGGCGAGAAGATCGCCGAAGCTCTGGACAAGGTCGGCCAGGACGG-- | 193 | 35 |
| FR54/e/1 | GGTTGGCGAGAAGATCGCCGAAGCTCTGGACAAGGTCGGCCAGGACGGT- | 176 | 36 |
| AF210319 | AGTCGGCGAGAAGATCGCCGAAGCTCTGGACAAGGTCGGCCAGGATGGCG | 700 | 37 |
| AF240571 | AGTCGGCGAGAAGATCGCCGAAGCTCTGGACAAGGTCGGCCAGGACGGTG | 262 | 38 |
| AY004277 | GGTTGGTGAGAAGATCGCCGAAGCCCTGGACAAGGTCGGCCAGGATGGCG | 262 | 39 |
| AF240568 | GGTTGGCGAGAAGATCGCCGAAGCCCTGGACAAGGTTGGCCAGGACGGCG | 263 | 40 |
| FR51/h/1 | GGTTGGCGAGAAGATCGCCGAAGCTCTGGACAAGGTCGGCCAGGACGG-- | 192 | 41 |
| FR59/b/2 | GGTTGGCGAGAAGATCGCCGAAGCTCTGGACAAGGTCGGCCAGGACGGT- | 180 | 42 |

Figure 3

SEQUENCE LISTING

<160> NUMBER OF SEQ ID NOS: 47

<210> SEQ ID NO 1
<211> LENGTH: 1428
<212> TYPE: DNA
<213> ORGANISM: Bifidobacterium psychraerophilum

<400> SEQUENCE: 1
gtcaggatga acgctggcgg cgtgcttaac acatgcaagt cgaacgggat ccatcaagct      60
tgcttgatgg tgagagtggc gaacgggtga gtaatacgtg actaacctgc ctcatacacc     120

-continued

```
ggaatagctc ctggaaacgg gtggtaatgc cggatgctcc aacatttcac atgttttgtt      180
gggaaagcgt tagcggtatg agatggggtc gcgtcctatc agcttgttgg tgaggtaatg      240
gctcaccaag gcttcgacgg gtagccggcc tgagagggcg accggccaca ttgggactga      300
gatacggccc agactcctac gggaggcagc agtggggaat attgcacaat gggcgaaagc      360
ctgatgcagc gacgccgcgt gcgggatgaa ggccttcggg ttgtaaaccg cttttaattg      420
ggagcaagcg agagtgagtg taccttttga ataagcaccg gctaactacg tgccagcagc      480
cgcggtaata cgtagggtgc aagcgttatc cggaattatt gggcgtaaag agctcgtagg      540
cggtttgtca cgcctggtgt gaaagtccat cgcttaacgg tggatctgcg ccgggtacgg      600
gcaggctaga gtgcagtagg ggagattgga attcccggtg taacggtgga atgtgtagat      660
atcgggaaga acaccaatgg cgaaggcaga tctctgggct gttactgacg ctgaggagcg      720
aaagcatggg gagcgaacag gattagatac cctggtagtc catgccgtaa acggtggatg      780
ctggatgtgg ggcccttcca cgggctccgt gtcggagcta acgcgttaag catcccgcct      840
ggggagtacg gccgcaaggc taaaactcaa agaaattgac gggggcccgc acaagcggcg      900
gagcatgcgg attaattcga tgcaacgcga gaaccttacc taggcttgac atgtttcgg       960 acagccccag agatggggtc tcccttcggg gccgattcac aggtggtgca tggtcgtcgt     1020
cagctcgtgt cgtgagatgt tgggttaagt cccgcaacga gcgcaaccct cgccttgtgt     1080
tgccagcacg ttatggtggg aactcacaag gaccgccgg ggttaactcg gaggaaggtg      1140
gggatgacgt cagatcatca tgcccttac gtctagggct tcacgcatgc tacaatggcc      1200
ggtacaacga gatgcgacat ggcgacatga agcgaatctc ttaaaaccgg tctcagttcg     1260
gattggagcc tgcaactcgg ctccatgaag gcggagtcgc tagtaatcgc gaatcagcaa     1320
cgtcgcggtg aatgcgttcc cgggccttgt acacaccgcc cgtcaagtca tgaaagtggg     1380
tagcacccga agccggtggc ctaaccttt ggagggagcc gtctaagg                   1428
```

<210> SEQ ID NO 2
<211> LENGTH: 1372
<212> TYPE: DNA
<213> ORGANISM: Bifidobacterium GC56

<400> SEQUENCE: 2

```
gtcgaacggg atccatcaag cttgcttgat ggtgagagtg cgaacgggt gagtaatgcg        60 tgactaacct gcctcataca ccggaatagc tcctggaaac gggtggtaat gccggatgct      120
ccaacatttc acatgttttg ttgggaaagc gttagcggta tgagatgggg tcgcgtccta      180
tcagcttgtt ggtgaggtaa tggctcacca aggcttcgac gggtagccgg cctgagaggg      240
cgaccggcca cattgggact gagatacggc ccagactcct acgggaggca gcagtgggga      300
atattgcaca atgggcgaaa gcctgatgca gcgacgccgc gtgcgggatg aaggccttcg      360
ggttgtaaac cgcttttaat gggagcaag cgagagtgag tgtaccttt gaataagcac       420 cggctaacta cgtgccagca gccgcggtaa tacgtagggt gcaagcgtta tccggaatta     480
ttgggcgtaa agagctcgta ggcggttttgt cacgcctggt gtgaaagtcc atcgcttaac    540
ggtggatctg cgccgggtac gggcaggcta gagtgcagta ggggagattg gaattcccgg     600
tgtaacggtg gaatgtgtag atatcgggaa gaacaccaat ggcgaaggca gatctctggg     660
ctgttactga cgctgaggag cgaaagcatg gggagcgaac aggattagat accctggtag     720
tccatgccgt aaacggtgga tgctggatgt gggacccttc cacgggtccc gtgtcggagc     780
taacgcgtta agcatcccgc ctggggagta cggccgcaag gctaaaactc aaagaaattg     840
```

```
acggggccc gcacaagcgg cggagcatgc ggattaattc gatgcaacgc gaagaacctt      900
acctaggctt gacatgtttc ggacagcccc agagatgggg tctcccttcg gggccgattc      960
acaggtggtg catggtcgtc gtcagctcgt gtcgtgagat gttgggttaa gtcccgcaac     1020
gagcgcaacc ctcgccttgt gttgccagca cgttatggtg ggaactcaca agggaccgcc     1080
ggggttaact cggaggaagg tggggatgac gtcagatcat catgccccct acgtctaggg     1140
cttcacgcat gctacaatgg ccggtacaac gagatgcgac atggcgacat gaagcgaatc     1200
tcttaaaacc ggtctcagtt cggattggag cctgcaactc ggctccatga aggcggagtc     1260
gctagtaatc gcgaatcagc aacgtcgcgg tgaatgcgtt cccgggcctt gtacacaccg     1320
cccgtcaagt catgaaagtg ggtagcaccc gaagccggtg gcctaacctt tt             1372

<210> SEQ ID NO 3
<211> LENGTH: 1356
<212> TYPE: DNA
<213> ORGANISM: Bifidobacterium GC56

<400> SEQUENCE: 3
atccatcaag cttgcttgat ggtgagagtg gcgaacgggt gagtaatgcg tgactaacct       60
gcctcataca ccggaatagc tcctggaaac gggtggtaat gccggatgct ccaacatttc      120
acatgttttg ttgggaaagc gttagccgta tgagatgggg tcgcgtccta tcagcttgtt      180
ggtgaggtaa tggctcacca aggcttcgac gggtagccgg cctgagaggg cgaccggcca      240
cattgggact gagatacggc ccagactcct acgggaggca gcagtgggga atattgcaca      300
atgggcgaaa gcctgatgca gcgacgccgc gtgcgggatg aaggccttcg ggttgtaaac      360
cgcttttaat tgggagcaag cgagagtgag tgtaccttt gaataagcac cggctaacta      420
cgtgccagca gccgcggtaa tacgtagggt gcaagcgtta tccggaatta ttgggcgtaa      480
agagctcgta gcggtttgt cacgcctggt gtgaaagtcc atcgcttaac ggtggatctg      540
cgccgggtac gggcaggcta gagtgcagta ggggagattg gaattcccgg tgtaacggtg      600
gaatgtgtag atatcgggaa gaacaccaat ggcgaaggca gatctctggg ctgttactga      660
cgctgaggag cgaaagcatg gggagcgaac aggattagat accctggtag tccatgccgt      720
aaacggtgga tgctggatgt gggacccttc cacgggttcc gtgtcggagc taacgcgtta      780
agcatcccgc ctggggagta cggccgcaag gctaaaactc aaagaaattg acggggccc      840 gcacaagcgg cggagcatgc ggattaattc gatgcaacgc gaagaacctt acctaggctt      900
gacatgtttc ggacagcccc agagatgggg tctcccttcg gggccgattc acaggtggtg      960
catggtcgtc gtcagctcgt gtcgtgagat gttgggttaa gtcccgcaac gagcgcaacc     1020
ctcgccttgt gttgccagca cgttatggtg ggaactcaca agggaccgcc ggggttaact     1080
cggaggaagg tggggatgac gtcagatcat catgccccct acgtctaggg cttcacgcat     1140
gctacaatgg ccggtacaac gagatgcgac atggcgacat gaagcgaatc tcttaaaacc     1200
ggtctcagtt cggattggag cctgcaactc ggctccatga aggcggagtc gctagtaatc     1260
gcgaatcagc aacgtcgcgg tgaatgcgtt cccgggcctt gtacacaccg cccgtcaagt     1320
catgaaagtg ggtagcaccc gaagccggtg gcctaa                                1356

<210> SEQ ID NO 4
<211> LENGTH: 1384
<212> TYPE: DNA
<213> ORGANISM: Bifidobacterium GC56

<400> SEQUENCE: 4
```

```
agggatccat caagcttgct tgatggtgag agtggcgaac gggtgagtaa tgcgtgacta      60
acctgcctca tacaccggaa tagctcctgg aaacgggtgg taatgccgga tgctccaaca     120
tttcacatgt tttgttggga aagcgttagc ggtatgagat ggggtcgcgt cctatcagct     180
tgttggtgag gtaatggctc accaaggctt cgacgggtag ccggcctgag agggcgaccg     240
gccacattgg gactgagata cggcccagac tcctacggga ggcagcagtg gggaatattg     300
cacaatgggc gaaagcctga tgcagcgacg ccgcgtgcgg gatgaaggcc ttcgggttgt     360
aaaccgcttt taattgggag caagcgagag tgagtgtacc ttttgaataa gcaccggcta     420
actacgtgcc agcagccgcg gtaatacgta gggtgcaagc gttatccgga attattgggc     480
gtaaagagct cgtaggcggt ttgtcacgcc tggtgtgaaa gtccatcgct taacggtgga     540
tctgcgccgg gtacgggcag gctagagtgc agtaggggag attggaattc ccggtgtaac     600
ggtggaatgt gtagatatcg gaagaacac caatggcgaa ggcagatctc tgggctgtta     660
ctgacgctga ggagcgaaag catggggagc gaacaggatt agataccctg gtagtccatg     720
ccgtaaacgg tggatgctgg atgtgggacc cttccacggg ttccgtgtcg gagctaacgc     780
gttaagcatc ccgcctgggg agtacggccg caaggctaaa actcaaagaa attgacgggg     840
gcccgcacaa gcggcggagc atgcggatta attcgatgca acgcgaagaa ccttacctag     900
gcttgacatg tttcggacag ccccagagat ggggtctccc ttcggggccg attcacaggt     960
ggtgcatggt cgtcgtcagc tcgtgtcgtg agatgttggg ttaagtcccg caacgagcgc    1020
aaccctcgcc ttgtgttgcc agcacgttat ggtgggaact cacaagggac cgccggggtt    1080
aactcggagg aaggtgggga tgacgtcaga tcatcatgcc ccttacgtct agggcttcac    1140
gcatgctaca atggccggta caacgagatg cgacatggcg acatgaagcg aatctcttaa    1200
aaccggtctc agttcggatt ggagcctgca actcggctcc atgaaggcgg agtcgctagt    1260
aatcgcgaat cagcaacgtc gcggtgaatg cgttcccggg ccttgtacac accgcccgtc    1320
aagtcatgaa agtgggtagc acccgaagcc ggtggcctaa ccttttggag ggagccgtct    1380
aagg                                                                  1384
```

<210> SEQ ID NO 5
<211> LENGTH: 20
<212> TYPE: DNA
<213> ORGANISM: Bifidobacterium GC56

<400> SEQUENCE: 5

```
aatagctcct ggaaacgggt                                                  20
```

<210> SEQ ID NO 6
<211> LENGTH: 20
<212> TYPE: DNA
<213> ORGANISM: Bifidobacterium GC56

<400> SEQUENCE: 6

```
cgtaagggc atgatgatct                                                   20
```

<210> SEQ ID NO 7
<211> LENGTH: 50
<212> TYPE: DNA
<213> ORGANISM: Bifidobacterium pseudocatenulatum

<400> SEQUENCE: 7

```
cgtcaccgcc ggctccaacc cgatcgcttt gcgtcgtggt atcgagaagg                 50
```

<210> SEQ ID NO 8

```
<210> SEQ ID NO 8
<211> LENGTH: 50
<212> TYPE: DNA
<213> ORGANISM: Bifidobacterium GC56

<400> SEQUENCE: 8
cgtcgttgcg ggctccaacc ccatcgctct tcgtcgcggc atcgagaagg            50

<210> SEQ ID NO 9
<211> LENGTH: 50
<212> TYPE: DNA
<213> ORGANISM: Bifidobacterium GC56

<400> SEQUENCE: 9
cgtcgttgcg ggctccaacc ccatcgctct tcgtcgcggc atcgagaagg            50

<210> SEQ ID NO 10
<211> LENGTH: 50
<212> TYPE: DNA
<213> ORGANISM: Bifidobacterium adolescentis

<400> SEQUENCE: 10
cgtcaccgcc ggttccaacc cgatcgcgct gcgtcgtggc atcgagaagg            50

<210> SEQ ID NO 11
<211> LENGTH: 50
<212> TYPE: DNA
<213> ORGANISM: Bifidobacterium ruminantium

<400> SEQUENCE: 11
cgtcaccgcc ggctccaacc cgatcgcgct gcgtcgcggc atcgaaaagg            50

<210> SEQ ID NO 12
<211> LENGTH: 50
<212> TYPE: DNA
<213> ORGANISM: Bifidobacterium merycicum

<400> SEQUENCE: 12
cgtggtcgcc ggctccaacc cgatcgctct gcgtcgcggt atcgagaagg            50

<210> SEQ ID NO 13
<211> LENGTH: 50
<212> TYPE: DNA
<213> ORGANISM: Bifidobacterium angulatum

<400> SEQUENCE: 13
cgtggtcgcc ggctccaacc cgattgcgct gcgccgcggc attgaaaagg            50

<210> SEQ ID NO 14
<211> LENGTH: 45
<212> TYPE: DNA
<213> ORGANISM: Bifidobacterium GC56
<220> FEATURE:
<221> NAME/KEY: misc_feature
<222> LOCATION: (11)..(11)
<223> OTHER INFORMATION: n is a, c, g, or t

<400> SEQUENCE: 14
cgtttgtggc nttagccatc gctcttcgtc gcggcatcga gaagg                 45

<210> SEQ ID NO 15
<211> LENGTH: 31
<212> TYPE: DNA
<213> ORGANISM: Bifidobacterium GC56

<400> SEQUENCE: 15
```
gccatcgctc ttcgtcgcgg catcgagaag g    31

<210> SEQ ID NO 16
<211> LENGTH: 50
<212> TYPE: DNA
<213> ORGANISM: Bifidobacterium pseudocatenulatum

<400> SEQUENCE: 16
cttccgaagc catcgtcaag gagcttatcg cagctgccaa ggacgttgag    50

<210> SEQ ID NO 17
<211> LENGTH: 50
<212> TYPE: DNA
<213> ORGANISM: Bifidobacterium GC56

<400> SEQUENCE: 17
cctcagacgc catcgtcaag gagctgattt ccgcagccaa ggacgttgag    50

<210> SEQ ID NO 18
<211> LENGTH: 50
<212> TYPE: DNA
<213> ORGANISM: Bifidobacterium GC56

<400> SEQUENCE: 18
cctcagacgc catcgtcaag gagctgattt ccgcagccaa ggacgttgag    50

<210> SEQ ID NO 19
<211> LENGTH: 50
<212> TYPE: DNA
<213> ORGANISM: Bifidobacterium adolescentis

<400> SEQUENCE: 19
ccgccgacgc catcgtcaag gaactcgtcg cagcggccaa ggacgttgag    50

<210> SEQ ID NO 20
<211> LENGTH: 50
<212> TYPE: DNA
<213> ORGANISM: Bifidobacterium ruminantium

<400> SEQUENCE: 20
cttccgacgc cattgtcaag gaacttgtcg cggccgccaa ggatgtcgag    50

<210> SEQ ID NO 21
<211> LENGTH: 50
<212> TYPE: DNA
<213> ORGANISM: Bifidobacterium merycicum

<400> SEQUENCE: 21
ccaccgaagt catcgtcaag gaactcgtcg ccgccgccaa ggacgtcgag    50

<210> SEQ ID NO 22
<211> LENGTH: 50
<212> TYPE: DNA
<213> ORGANISM: Bifidobacterium angulatum

<400> SEQUENCE: 22
ccgccgacgc catcgtcaag gaactcgtcg cagccgccaa ggacgtcgag    50

<210> SEQ ID NO 23
<211> LENGTH: 49
<212> TYPE: DNA
<213> ORGANISM: Bifidobacterium GC56

<400> SEQUENCE: 23
ctcagacgcc atcgtcaagg agctgatttc cgcagccaag gacgttgag    49

<210> SEQ ID NO 24
<211> LENGTH: 50
<212> TYPE: DNA
<213> ORGANISM: Bifidobacterium GC56

<400> SEQUENCE: 24
cctcagacgc catcgtcaag gagctgattt ccgcagccaa ggacgttgag    50

<210> SEQ ID NO 25
<211> LENGTH: 50
<212> TYPE: DNA
<213> ORGANISM: Bifidobacterium pseudocatenulatum

<400> SEQUENCE: 25
accaaggatc agatcgccgc taccgcaacg atttccgccg ccgatccgga    50

<210> SEQ ID NO 26
<211> LENGTH: 50
<212> TYPE: DNA
<213> ORGANISM: Bifidobacterium GC56

<400> SEQUENCE: 26
accaaggatc agatcgccgc gacggcaacg atctccgcgg ccgatcccga    50

<210> SEQ ID NO 27
<211> LENGTH: 50
<212> TYPE: DNA
<213> ORGANISM: Bifidobacterium GC56

<400> SEQUENCE: 27
accaaggatc agatcgccgc gacggcaacg atctccgcgg ccgatcccga    50

<210> SEQ ID NO 28
<211> LENGTH: 50
<212> TYPE: DNA
<213> ORGANISM: Bifidobacterium adolescentis

<400> SEQUENCE: 28
accaaggatc agatcgctgc caccgcaacg atctccgccg ctgatccgga    50

<210> SEQ ID NO 29
<211> LENGTH: 50
<212> TYPE: DNA
<213> ORGANISM: Bifidobacterium ruminantium

<400> SEQUENCE: 29
accaaggacc agatcgctgc caccgcaacg atctccgccg ctgatccgga    50

<210> SEQ ID NO 30
<211> LENGTH: 50
<212> TYPE: DNA
<213> ORGANISM: Bifidobacterium merycicum

<400> SEQUENCE: 30
accaaggatc agatcgctgc cactgctacg atctccgccg ccgatcctga    50

<210> SEQ ID NO 31
<211> LENGTH: 50
<212> TYPE: DNA
<213> ORGANISM: Bifidobacterium angulatum

<400> SEQUENCE: 31
accaaggatc agatcgctgc caccgcaacg atttccgccg ccgatcccga    50

<210> SEQ ID NO 32
<211> LENGTH: 50
<212> TYPE: DNA
<213> ORGANISM: Bifidobacterium GC56

<400> SEQUENCE: 32
accaaggatc agatcgccgc gacggcaacg atctccgcgg ccgatcccga    50

<210> SEQ ID NO 33
<211> LENGTH: 50
<212> TYPE: DNA
<213> ORGANISM: Bifobacterium GC56

<400> SEQUENCE: 33
accaaggatc agatcgccgc gacggcaacg atctccgcgg ccgatcccga    50

<210> SEQ ID NO 34
<211> LENGTH: 50
<212> TYPE: DNA
<213> ORGANISM: Bifidobacterium pseudocatenulatum

<400> SEQUENCE: 34
agtcggcgag aagatcgccg aagctcttga caaggttggc caggacggcg    50

<210> SEQ ID NO 35
<211> LENGTH: 48
<212> TYPE: DNA
<213> ORGANISM: Bifidobacterium GC56

<400> SEQUENCE: 35
ggttggcgag aagatcgccg aagctctgga caaggtcggc caggacgg    48

<210> SEQ ID NO 36
<211> LENGTH: 49
<212> TYPE: DNA
<213> ORGANISM: Bifidobacterium GC56

<400> SEQUENCE: 36
ggttggcgag aagatcgccg aagctctgga caaggtcggc caggacggt    49

<210> SEQ ID NO 37
<211> LENGTH: 50
<212> TYPE: DNA
<213> ORGANISM: Bifidobacterium adolescentis

<400> SEQUENCE: 37
agtcggcgag aagatcgccg aagctctgga caaggtcggc caggatggcg    50

<210> SEQ ID NO 38
<211> LENGTH: 50
<212> TYPE: DNA
<213> ORGANISM: Bifidobacterium ruminantium

<400> SEQUENCE: 38
agtcggcgag aagatcgccg aagctctgga caaggtcggc caggacggtg    50

<210> SEQ ID NO 39
<211> LENGTH: 50
<212> TYPE: DNA
<213> ORGANISM: Bifidobacterium merycicum

<400> SEQUENCE: 39

-continued ggttggtgag aagatcgccg aagccctgga caaggtcggc caggatggcg         50

<210> SEQ ID NO 40
<211> LENGTH: 50
<212> TYPE: DNA
<213> ORGANISM: Bifidobacterium angulatum

<400> SEQUENCE: 40
ggttggcgag aagatcgccg aagccctgga caaggttggc caggacggcg         50

<210> SEQ ID NO 41
<211> LENGTH: 48
<212> TYPE: DNA
<213> ORGANISM: Bifidobacterium GC56

<400> SEQUENCE: 41
ggttggcgag aagatcgccg aagctctgga caaggtcggc caggacgg           48

<210> SEQ ID NO 42
<211> LENGTH: 49
<212> TYPE: DNA
<213> ORGANISM: Bifidobacterium GC56

<400> SEQUENCE: 42
ggttggcgag aagatcgccg aagctctgga caaggtcggc caggacggt          49

<210> SEQ ID NO 43
<211> LENGTH: 23
<212> TYPE: DNA
<213> ORGANISM: Bifidobacterium GC56

<400> SEQUENCE: 43
atttccgcag ccaaggacgt tga                                      23

<210> SEQ ID NO 44
<211> LENGTH: 20
<212> TYPE: DNA
<213> ORGANISM: Bifidobacterium GC56

<400> SEQUENCE: 44
atttccgcag ccaaggacgt                                          20

<210> SEQ ID NO 45
<211> LENGTH: 21
<212> TYPE: DNA
<213> ORGANISM: Bifidobacterium GC56

<400> SEQUENCE: 45
tccagagctt cggcgatctt c                                        21

<210> SEQ ID NO 46
<211> LENGTH: 20
<212> TYPE: DNA
<213> ORGANISM: Bifidobacterium
<220> FEATURE:
<221> NAME/KEY: misc_feature
<223> OTHER INFORMATION: s = g or c; y = c or t; r=g or a

<400> SEQUENCE: 46
gtscaygarg gyctsaagaa                                          20

<210> SEQ ID NO 47
<211> LENGTH: 20
<212> TYPE: DNA
<213> ORGANISM: Bifidobacterium

```
<400> SEQUENCE: 47
cgtaaggggc atgatgatct                                                    20
```

PROBIOTIC BIFIDOBACTERIAL SPECIES

The invention relates to a bacterium belonging to the genus *Bifidobacterium*, to probiotic compositions comprising said bacterium, particularly food products, and to their use in the treatment of gastrointestinal diseases.

BACKGROUND TO THE INVENTION

Bifidobacteria (or bacteria belonging to the *Bifidobacterium* genus) constitute one of the most important populations of human and animal faecal flora. It is generally considered an indication of good health when these bacteria are present at a high rate in faecal flora. For this reason, they are known as probiotic bacteria (beneficial microorganisms which improve the natural balance of intestinal flora when ingested alive). Examples of known Bifidobacteria include *B. adolescentis, B. animalis, B. bifidum, B. breve, B. catenulatum* and *B. longum* and these bacteria have been shown to have beneficial technological, organoleptic and probiotic effects.

Bifidobacteria are most commonly found as an additive in fermented milks (yoghurts with "active Bifidus") and thus constitute an economically important commodity. The strains chosen by the milk industry must meet numerous strict requirements, such as resistance to the process of manufacture and survival within the foodstuff. The most commonly used species in France are *B. animalis* subsp. *lactis* and *B. animalis* subsp. *animalis*, which is a subspecies from animal origin, never isolated from humans. In view of the importance of bifidobacteria, there is a great need to identify novel species within this genus having properties optimally matched to the requirements of the food industry. For example, in 2004, a group identified and isolated *Bifidobacterium psychraerophilum* from a porcine caecum (Simpson, P. J. et al. (2004) Int J Syst Evol Microbiol 54: 401-6). Previously known *Bifidobacterium* species had only been able to grow at temperatures between 20° C. and 46-49.5° C. (Biavati, B. et al., (2000), Annals of Microbiology 50: 117-131; Dong et al., (2000) Int J Syst Evol Microbiol 50 Pt 1: 119-25), however, this bacterium demonstrated an advantage over all previous species by growing at between 4 and 10° C. This is beneficial for probiotic compositions as the bacteria are more likely to survive the low storage temperatures and would therefore prolong shelf-life. There is thus a great need for the identification of further bifidobacterial species, which not only possess unique advantages but also retain the benefits of previously identified bifidobacterial species.

SUMMARY OF THE INVENTION

Thus, according to a first aspect of the invention there is provided *Bifidobacterium* GC56 strain FR62/b/3, deposited at the Collection Nationale de Cultures de Micro-organismes (CNCM, Institut Pasteur) on 9 Dec. 2004 with accession number CNCM I-3342, or a homolog, descendant or mutant thereof.

It will be appreciated that a homolog of *Bifidobacterium* GC56 will be understood to refer to any bifidobacteria strain having DNA sequence homology of greater than 40% with *Bifidobacterium* GC56 strain FR62/b/3 deposited at the Collection Nationale de Cultures de Micro-organismes (CNCM, Institut Pasteur) on 9 Dec. 2004, with accession number CNCM I-3342 (hereinafter referred to as 'GC56'). Preferably, a GC56 homolog is one having greater than 50% homology with GC56, more preferably greater than 60%, most preferably greater than 70%, especially preferably greater than 80% or most especially preferably greater than 90% (or any range between any of the above values). It will also be appreciated that sequence homology can be tested as described herein with reference to DNA-DNA reassociation experiments. Such experiments may include detection of specific sequences of 16S rDNA or of the hsp60 gene and these sequences and linked endonuclease restriction sites allow the detection of GC56. Other experiments, which may also identify GC56, include ELISA-PCR and PCR-RFLP.

GC56 represents a new species of *Bifidobacterium* called *Bifidobacterium crudilactis*. The terms GC56, GC56 group, *Bifidobacterium* GC56 and *Bifidobacterium crudilactis* are used interchangeably to refer to this new species of *Bifidobacterium*.

Examples of strains of GC56 discussed herein include FR62/b/3, FR59/b/2, and FR47/3. The 16S rDNA gene sequences of these strains have been deposited in GenBank and have the accession numbers: AY952449 (Sequence ID No: 3), AY952448 (Sequence ID No: 4) and AY952450 (Sequence ID No: 2) respectively. The 16S rDNA gene sequence for AY952448 deposited at GenBank has an error at the application date of the present application. The inventors have applied to correct the error in the sequence.

GC56 was identified during the cheese making of "L'étoile du Vercors" which is a traditional and manual process. GC56 is present throughout the cheese production process (i.e. from raw milk to the end of maturing), with a statistically significant increase during the process. These bacteria belong to a natural microbial population which takes part in the development of organoleptic properties of the end product.

GC56 has the key advantage of being the first bifidobacterial species isolated from a food production process whereas previous bifidobacteria have been extracted from the digestive tracts of humans or animals, thus GC56 is easier to integrate into the manufacturing process and is also easier to stabilise in food and fermented products than other bifidobacteria.

GC56 has also been found to be psychotrophic and to be able to grow at temperatures as low as 10-12° C., the maturing temperature of the "L'étoile du Vercors" process, whereas most others need a temperature of more than 20° C. GC56 is thought to constitute a milk subdominant population selected by the low temperature of the L'étoile du Vercors process (milk at 4° C., warmed to 22° C. until the removal from the mould at Day 2, then maintained at 12° C. from the maturing at Day 8 until Day 28). The key advantage of growth at low temperatures is that GC56 bacteria are more likely to survive low storage temperatures than most other probiotic bacterial compositions, which would therefore prolong the shelf-life.

A further advantage of GC56 is that it is aero-tolerant, whereas most others need strict anaerobiotic conditions to multiply and survive.

Further advantages of *Bifidobacterium* GC56 are that they provide a good fermentation of milk (alone or in a mix), a good resistance to lactic acid in the end product (more than $10^6$ cfu/g), a sufficient growth rate, a good resistance to stomach acidity, the biliary salts and to the intestinal enzymes and a lower need for growth factors (yeast extract, hydrolysed protein, vitamins and other elements).

As a second aspect of the invention there is provided a probiotic composition comprising *Bifidobacterium* GC56 as hereinbefore defined and one or more acceptable excipients.

It will be appreciated that an acceptable excipient will be well known to the person skilled in the art of probiotic composition preparation. Examples of such acceptable excipients include: sugars such as sucrose, isomerized sugar, glucose, fructose, palatinose, trehalose, lactose and xylose; sugar alcohols such as sorbitol, xylitol, erythritol, lactitol, palatinol, reduced glutinous starch syrup and reduced glutinous maltose syrup; emulsifiers such as sucrose esters of fatty acid, glycerin esters of fatty acid and lecithin; thickeners (stabilizers) such as carrageenan, xanthan gum, guar gum, pectin and locust bean gum; acidifiers such as citric acid, lactic acid and malic acid; fruit juices such as lemon juice, orange juice and berry juice; vitamins such as vitamin A, vitamin B, vitamin C, vitamin D and vitamin E; and minerals such as calcium, iron, manganese and zinc.

Compositions of the invention may be prepared by admixture, suitably at ambient temperature and atmospheric pressure, usually adapted for oral administration. Such compositions may be in the form of tablets, capsules, oral liquid preparations, conventional food products, powders, granules, lozenges, reconstitutable powders or suspensions.

Tablets and capsules for oral administration may be in unit dose form, and may contain one or more conventional excipients, such as binding agents, fillers, tabletting lubricants, disintegrants, and acceptable wetting agents. The tablets may be coated according to methods well known in pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and if desired, conventional flavourings or colourants.

In one preferred embodiment, the composition of the invention is formulated as a conventional food product, more preferably, a dairy based product (e.g. fermented milk, vegetable milk, soybean milk, butter, cheese or yoghurt) or fruit juice. The composition is preferably formulated as a food or drink for adult and infant humans and animals. In an alternatively preferred embodiment, the composition is formulated as a lyophilised or spray-dried powder.

As well as exhibiting a probiotic effect (i.e. maintaining the balance of intestinal flora), bifidobacteria are also generally believed to be of potential use in the treatment and/or prophylaxis of a variety of disorders, such as gastrointestinal diseases (e.g. diarrhoea), cancer, cholesterol excesses, allergies and infection.

Thus, as a further aspect of the invention, there is provided *Bifidobacterium* GC56 for use as a therapeutic substance, in particular in the treatment and/or prophylaxis of the above disorders.

The invention further provides a use of *Bifidobacterium* GC56 in the preparation of a medicament for the treatment and/or prophylaxis of the above disorders.

The invention further provides a method of treatment and/or prophylaxis of the above disorders, in a human or animal subject, which comprises administering to the subject a therapeutically effective amount of *Bifidobacterium* GC56.

*Bifidobacterium* GC56 may be used in combination with other therapeutic agents, for example, other medicaments known to be useful in the treatment and/or prophylaxis of gastrointestinal diseases (e.g. diarrhoea), cancer, cholesterol excesses, allergies and infection.

Thus, as a further aspect of the invention, there is provided a combination comprising *Bifidobacterium* GC56 together with a further therapeutic agent or agents.

The combinations referred to above may conveniently be presented for use in the form of a probiotic composition and thus probiotic compositions comprising a combination as defined above together with one or more excipients comprise a further aspect of the invention. The individual components of such combinations may be administered either sequentially or simultaneously in separate or combined probiotic compositions.

In a preferred embodiment, *Bifidobacterium* GC56 is combined with other bifidobacteria or other probiotic bacteria such as: bacteria belonging to the genus *Lactobacillus* such as *Lactobacillus acidophilus, Lactobacillus gasseri, Lactobacillus plantarum, Lactobacillus buchneri, Lactobacillus casei, Lactobacillus johnsonii, Lactobacillus gallinarum, Lactobacillus amylovorus, Lactobacillus brevis, Lactobacillus rhamnosus, Lactobacillus kefir, Lactobacillus paracasei, Lactobacillus crispatus, Lactobacillus delbrueckii* subsp. *delbrueckii, Lactobacillus delbrueckii* subsp. *bulgaricul, Lactobacillus helveticus, Lactobacillus zeae* and *Lactobacillus salivalius*; bacteria belonging to the genus *Streptococcus* such as *Streptococcus thermophilus*; bacteria belonging to genus *Lactococcus* such as *Lactococcus lactis* subsp. *cremoris* and *Lactococcus lactis* subsp. *lactis*; bacteria belonging to the genus *Bacillus* such as *Bacillus subtilis*; and yeast belonging to the genus *Saccharomyces, Torulaspora* and *Candida* such as *Saccharomyces cerevisiae, Torulaspora delbrueckii* and *Candida kefyr*.

DETAILED DESCRIPTION OF THE INVENTION

Preferred embodiments of the invention will now be described merely by way of example with reference to the accompanying drawings in which:

FIG. 1 shows the phylogenetic tree of *Bifidobacterium* 16S rDNA sequences (1419 nucleotides) including FR62/b/3 strain (Genbank Accession No. AY952449), FR47/3 strain (Genbank Accession No. AY952450), FR59/b/2 strain (Genbank Accession No. AY952448). FR62/b/3, FR47/3 and FR59/b/2 are all strains of *Bifidobacterium crudilactis*. The sequences were aligned with ClustalX. The tree was rooted with *Actinomyces bovis* and constructed using a neighbour-joining algorithm. Bootstrap values, calculated from 1000 trees, are given at each node. Numbers in parenthesis correspond to the GenBank accession numbers;

FIG. 2 shows sequence alignments of 16S rDNA of GC56 FR62/b/3, Fr47/3 and Fr59/b/2 strains with *B. psychraerophilum*. The sequences were aligned using the program ClustalW from the European Bioinformatics Institute.

Sequence 1 (Sequence ID No: 1) is *B. psychraerophilum* (AY174108), Sequence 2 (Sequence ID No: 2) is GC56 FR47/3 (AY952450), Sequence 3 (Sequence ID No: 3) is GC56 FR62/b/3 (AY952449) and Sequence 4 (Sequence ID No: 4) is GC56 FR59/b/2 (AY952448). Sequence C is the consensus sequence. In the consensus sequence the following symbols are used "." if majority character has a representation>=20% in the sequences; ":" if majority character has a representation>=40% in the sequences; "+" if majority character has a representation>=60% in the sequences; "*" if majority character has a representation>=80% in the sequences; and the character itself, if this is present in all the sequences.

Figure 4:
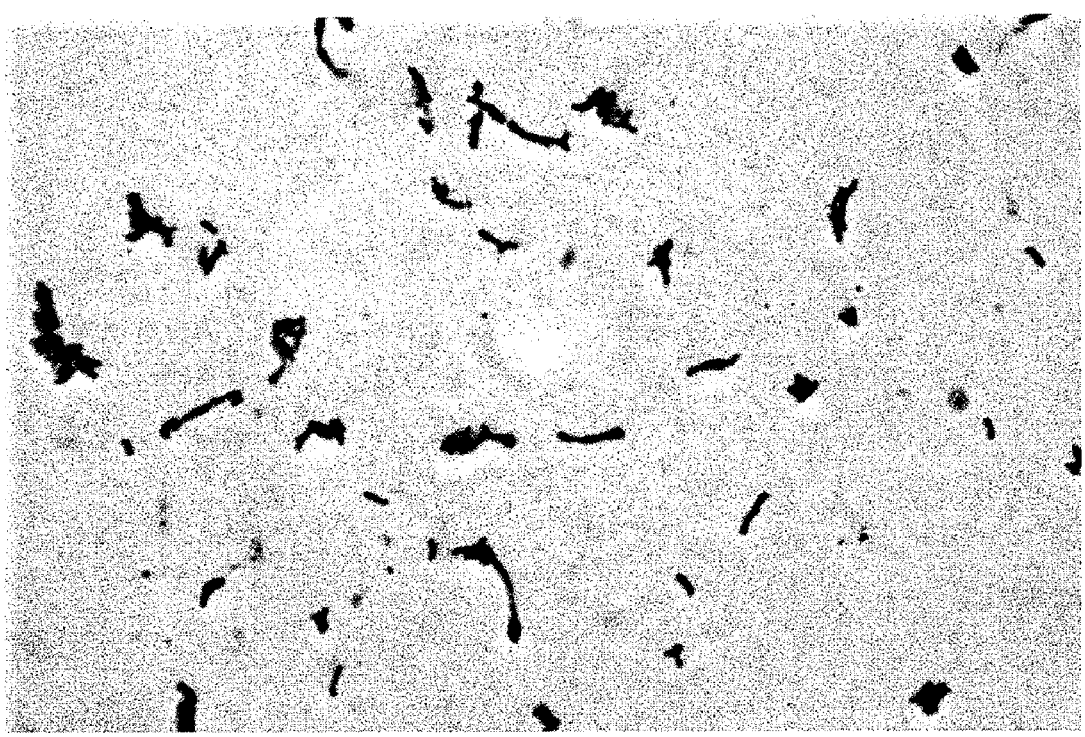

The restriction map between 16S rDNAup (5'-aatagctcctg-gaaacgggt-3' (Sequence ID No: 5)) and 16S rDNAdwn (5'-cgtaaggggcatgatgatct-3' (Sequence ID No: 6)) includes: AluI: AGCT cut positions 5, 100, 411, 696, 902 (underlined) and TaqI: TCGA cut positions 132, 796 (italics);

FIG. 3 shows an hsp60 gene sequence alignment of several strains of the GC56 group with closely identified sequences. More specifically, FIG. 3 show the alignment of partial sequences of the hsp60 gene of 4 of the GC56 group (FR47/3, FR51/h/1, FR54/e/1, 59/b/2) with closely identified sequences found on Genbank (PubMed-BLAST), namely: *B. pseudocatenulatum* (AY004274), *B. adolescentis* (AF210319), *B. ruminantium* (AF240571), *B. merycicum* (AY004277), *B. angulatum* (AF240568). FAM-ATTTCCG-CAGCCAAGGACGTTGA-DQ (Sequence ID No: 43): is a probe used for targeting the hsp60 gene and is specific of the GC56 group. 5'-ATTTCCGCAGCCAAGGACGT-3' (Sequence ID No: 44) and 5'-TCCAGAGCTTCGGC-GATCTTC-3' (Sequence ID No: 45): are forward and reverse primers specific to the GC56 group used for targeting the hsp60 gene; and FIG. 4 shows the morphological appearance of GC56.

Isolation of Bifidobacterium GC56

GC56 was isolated from a raw milk cheese process in the industry "L'étoile du Vercors" (France). Cultural methods (Delcenserie et al., (2005) J Microbiol Methods 61: 55-67), but particularly molecular methods, allowed detection of these bacteria throughout the production chain of the product and the checking of the composition of the end products. 95 strains were isolated from 31/31 studied cheeses "L'Etoile du Vercors" at different stages of the production, in 3/7 cheeses from trade raw milk cheeses other than those from "L'Etoile du Vercors" and in raw milk samples. *Bifidobacterium* GC56 strain FR62/b/3 (=CUETM 04/3) has been deposited at the Collection Nationale de Cultures de Micro-organismes (CNCM, Institut Pasteur) on 9 Dec. 2004 with accession number CNCM I-3342 and the sequence has been deposited on Genbank with accession number AY952449.

Detection of *Bifidobacterium* GC56 by PCR

1. Preparation of DNA Targets

DNA-extraction (Wizard® genomic DNA purification kit of Promega): One millilitre broth was centrifuged for 2 min. at 13000 g. The pellet was suspended in 480 µl EDTA, 60 µl of lysozyme, and 120 µl of cellular lysis solution and incubated for 45 min at 37° C. After centrifugation, 600 µl of nuclei lysis solution was added to the pellet followed by incubation for 5 min at 80° C. When cooled, 200 µl of protein lysis solution was added followed by vortexing. The resultant suspension was then incubated for 5 min on ice and was centrifuged for 5 min at 13000 g. The supernatant was transferred to a clean tube containing 600 µl of isopropanol and the tube was then centrifuged. The supernatant was decanted and 600 µl ethanol 70% was added and the tube centrifuged. The ethanol was aspirated and pellet air-dried for 10 min. Finally, the DNA pellet was rehydrated in 100 µl of rehydration solution overnight at 4° C.

2. PCR Protocols

GC56 can be detected within a complex microbial population by using two PCR methodologies based on the hsp60 gene:

(a) PCR Using Species Specific Primers

Four microliters DNA (50-100 ng), 0.2 µl (400 pmoles/l) of the upstream primer 5'-ATTTCCGCAGCCAAGGACGT-3' (Sequence ID No: 44); Table 1) and 0.2 µl (400 pmoles/l) of the downstream primer (5'-TCCAGAGCTTCGGC-GATCTTC-3' (Sequence ID No: 45); Table 1), 0.2 mol/l dNTP, 0.2 µl (1U) Taq polymerase enzyme, 2 µl enzyme buffer, 1.6 µl MgCl$_2$ and 11.0 µl ultra-pure water were mixed to achieve a total volume of 20 µl.

The thermal-cycler was programmed as follows: one 10 minute cycle at 95° C. followed by 30 cycles composed of 30 seconds at 95° C., 30 seconds at 64.2° C. (annealing temperature) and 30 seconds at 72° C. and ended by 5 minutes at 72° C.

Twenty micro-liters of each PCR-product were added to 2 µl of colouring agent and transferred to a well of a 2% agarose-agar gel. The size evaluation was made using a Smart Ladder®. The agar was immersed in TAE 1× buffer and migration conditions were of 60 min at 120V at 400 mA. After migration, the agar was incubated for 10 min in ethidium bromide and washed for 10 min under water. The amplification products were observed under ultra-violet trans-illumination. The hsp60 gene sequence was identified by correlating the position with the Smart Ladder®. A blank control well was also made to evaluate contamination in each PCR.

(b) Real-Time PCR Using Species Specific Probe

A pair of degenerate primers specific to the Bifidobacterium genus (Table 1) were used for the PCR on the hsp60 gene. One probe was chosen from hsp60 sequences of the GC56 group (Table 1) after DNA sequencing of 4 strains of the GC56 group (FR51/h/1, FR47/3b, FR59/b/2, FR54/e/1). The bifidobacteria sequences were aligned using the program ClustalW from the European Bioinformatics Institute. The alignments revealed specific sequences for the GC56 group.

From these sequences, probes were derived using the primers and probes design guidelines provided by Applied Biosystems (Applied Biosystems, Foster city, USA). To check for specificity, the selected probes were compared to all available hsp60 gene sequences using the BLAST database search program. The GC56 probe was labelled with a carboxvfluorescein (FAM) (a reporter dye) and DQ™.

TABLE 1

Primers and probes used for amplification of *bifidobacteria* and identification of the GC56 group.

| Target organism(s) | Primers/ probes | Targeted gene | Sequence (5'-3') | Amplicon size | Reference |
|---|---|---|---|---|---|
| *Bifidobacterium* spp. | Forward primer | hsp60 gene | GTSCAYGARGGYCTSAAGAA (Seq ID No: 46) | 217 bp | Delcenserie et al. (2004) |
| | Reverse primer | | CGTAAGGGGCATGATGATCT (Seq ID No: 47) | | |
| GC56 group | Forward primer | hsp60 gene | 5'-ATTTCCGCAGCCAAGGACGT-3' (Seq ID No: 44) | 105 bp | This study |
| | Reverse primer | | 5'-TCCAGAGCTTCGGCGATCTTC-3' (Seq ID No: 45) | | |

TABLE 1-continued

Primers and probes used for amplification of bifidobacteria and identification of the GC56 group.

| Target organism(s) | Primers/ probes | Targeted gene | Sequence (5'-3') | Amplicon size | Reference |
|---|---|---|---|---|---|
| GC56 group | Probe | hsp60 gene | FAM-ATTTCCGCAGCCAAGGACGTTGA-DQ (Seq ID No: 43) | | This study |

Sensitivity and Specificity of the Assays

To check the specificity of the probe, PCR was performed on 55 strains belonging to 13 different *Bifidobacterium* species and 9 *Bifidobacterium* strains belonging to the GC56 group. The results observed with the GC56 probe revealed a specificity of 98% (only one *B. adolescentis* strain (5031e), was positive) and a sensitivity of 100% (the 9 tested strains from the GC56 group were positive).

Real-Time PCR Conditions

Amplification reaction mixtures contained 10 to 50 ng of DNA, 12.5 µl of qPCR™ Mastermix (Eurogentec, Seraing, Belgium), 960 nM of each primer, 50 to 150 nM of fluorogenic probe and 5 mM $MgCl_2$ in a total volume of 25 µl. In each microwell plate, one well was used as non-template control, which contained all the reagents except the DNA sample. The amplification, 50° C. for 2 min, 95° C. for 10 min, and then 40 cycles of two-temperature PCR (95° C. for 30 s and 60° C. for 90 s) and detection was carried out on an ABI Prism 7000 sequence detection system (Applied Biosystems, Foster city, USA). The PCR results for the samples were expressed as deltaRn (relative sensitivity) fluorescence signal.

A sample was considered as positive when the Ct value was lower than 25 for a relative fluorescence value higher than 500.

Other variations of these methods such as PCR-multiplex, Real-time PCR could be used as well as other techniques such as hybridization techniques, dot-blot hybridization, fluorescent in situ hybridization, colony hybridization, restriction fragment length polymorphism analysis.

Characterisation of *Bifidobacterium* GC56

(a) Temperature

In a preliminary study, strain FR62/b/3 of GC56 was incubated in 10 ml of full-cream milk, full-cream milk with milk powder (to reach 15% protein in dry matter), half-skimmed milk, half-skimmed milk with milk powder and sweetened concentrated milk (Nestlé®). UHT milk and Nestlé® milk powder were used. Inoculated milk samples were incubated in anaerobiotic jars at 30 and 37° C. for 72 hours and bacteria were then counted. Growth rate was found to be better at 30° C. than at 37° C. so 30° C. was chosen for further studies.

(b) Growth

Bifidobacteria were subcultured in BHI (double concentration) broth at 30° C. during 3 days in anaerobiotic conditions. Initial concentration in broth was of $10^7$ cfu/ml. The broth was diluted in peptone-saline water from ten to ten. One hundred micro-litres of broth and dilutions −2, −4, −6 and −8 were harvested and suspended in 10 ml of full-cream milk or full-cream milk with milk powder (to reach 15% protein in dry matter). The milks were incubated in anaerobic jars for 6, 12, 24 and 48 hours at 30° C. At each incubation time, pH was measured and the bacteria counted with a spiral sowing.

Results showed better growth in complemented milk: The bacterial concentration arose $10^{10}$ cfu/ml after 48 hours with an initial inoculation of $10^5$, $10^3$ and $10^1$ cfu/ml and $10^9$ with an initial inoculation of $10^{-1}$ cfu/ml. The pH values tended to 4.6-5.3 in all the complemented milk.

In full-cream milk only $10^9$ cfu/ml were produced from the initial rate of $10^5$ cfu/ml and $10^6$ from $10^3$ cfu/ml. The pH decrease reached 5.7-6.4.

The aim of this preliminary study was to know the needed initial concentration and to study the evolution of the fermentation process.

Then, an innoculum of strain FR62/b/3 (9.5 log cfu/ml from a based milk medium) was cultured at 30° C. during 24 hours in a 20 L fermentation vat containing milk based medium (0.3% Peptone-casein, 0.5% Yeast extract and 8% Skimmed milk powder). Eight 50 ml samples were harvested at the following times: inoculation time and after 2, 4, 6, 8, 10, 12 and 24 incubation hours. Spiral sowing was straight made for each sample. The pH was followed automatically in the fermentation vat.

The results showed a growth from 8.4 log cfu/ml (inoculation time) to 9.2 after 6 hours and this rate was maintained until 24 hours.

When inoculated with a *Lactobacillus acidophilus* strain, the FR62/b/3 strain grew from 8.1 log cfu/ml (inoculation time) to 9.2 after 10 hours and we observed a rate of 8.9 log cfu/ml after 24 hours although the pH decreased more than when it was alone (see section (c) below).

GC56 is also able to multiply in TPY broth (in bain-marie) up to a maximum temperature of 41.5° C. and a minimum temperature of 7° C., the optimum temperature for growth is 39° C. In TPY, the minimum initial pH for growth is 4.7. GC56 is also able to multiply on TPY agar under aerobic conditions at 37° C. and 39° C.

Colonies of GC56 on TPY agar at 39° C. under anaerobic conditions are cream, circular, and convex with entire edges. They reach a diameter of up 1 mm. They reach a reduced diameter (less than 1 mm) under aerobic conditions.

(c) pH

The milk media pH was initially 6.6.

When cultured alone in the fermentation vat, strain FR62/b/3 of GC56 produced a pH decrease from 5.9 (at inoculation time) to 5.0 after 6 hours, 4.2 after 12 hours and 3.9 after 24 hours.

In the presence of the *Lactobacillus acidophilus* strain, which further acidifies the medium, the pH values decreased from 5.9 to 4.4 after 6 hours, 3.8 after 12 hours and 3.5 after 24 hours. The bacterial counts of the 2 species increased to 8 log cfu/ml after 24 hours.

(d) Survival

After incubation in a fermentation vat, the survival in refrigerator conditions (aerobic conditions, temperature between 4-8° C.) was studied.

From an initial rate of 9.2 log cfu/ml, strain FR62/b/3 of GC56 reached 8.5 log cfu/ml after 18 days and 7.3 log cfu/ml after 29 days. According to the literature, a rate greater than $10^6$ or $10^7$ cfu/ml or /g of probiotics in the product is required to allow observation of positive effects.

(e) Biochemical Analysis

The GC56 group is well phenotypically individualized by numerical analysis (classification based on unweighted average linkage and Hartigan's clustering methods). No type or reference strains belonging to another species of the *Bifidobacterium* genus join the group.

Biochemical characteristics which differentiate the GC56 group and the species *B. pseudolongum* the most frequently isolated species in raw milk and in raw milk cheeses are presented in Table 2 below which shows the percentage of positives for certain defined characteristics:

TABLE 2

| Characteristics | GC56 group (138 strains) | *B. pseudolongum* (98 strains) |
|---|---|---|
| Fermentation: | | |
| Ribose | 96 | 43 |
| Alpha-methyl-D-glucoside | 66 | 10 |
| Esculine | 99 | 51 |
| Starch | 0 | 94 |
| Glycogen | 0 | 90 |
| Enzymatic tests: | | |
| Beta-glucosidase | 93 | 47 |
| Glycine arylamidase | 86 | 47 |

Phenotypic characteristics that differentiate the new strain isolates of *Bifidobacterium crudilactis* from *B. psychraerophilum*, the closest phylogenetically species, are presented in Table 3. The data in Table 3 are based on 141 different isolates of *B. crudilactis*. The results are given as the percentage of positive responses observed in the 141 isolates, FR62/b/3T (a strain of *B. crudilactis*), and *B. psychraerophilum* LMG 21775T.

TABLE 3

| Characteristics | *B. crudilactis* (141 strains) | *B. crudilactis* FR62/b/3$^T$ (LMG P-22559$^T$) | *B. psychraerophilum* LMG 21775$^T$ (Simpson et al., 2004) |
|---|---|---|---|
| Acidification of: | | | |
| L-arabinose | 1 | − | + |
| Amygdalin | 13 | − | + |
| Arbutin | 1 | − | + |
| Salicin | 2 | − | + |
| Lactose | 100 | + | − |
| Melezitose | 1 | − | + |
| Enzymatic test: | | | |
| Alpha-arabinosidase | 1 | − | + |
| Maximum growth temperature* | — | 41.5° C. (6 days) | 42° C. |
| Minimum growth temperature† | — | 7° C. (6 weeks) | 4° C. |
| Minimum growth pH | | 4.7 | 4.5 |
| DNA G + C content (mol %) | 55.2 (9 strains) (SD = 0.83) | 56.4 (4 experiments) (SD = 0.60) | 59.2 (HPLC, Simpson et al., 2004 Int J Syst Evol Microbiol 54, 401-6) 55.7 ($T_m$‡) |

Legend of Table 3:
*growth within 8 days;
†within 4 weeks;
‡mean of 2 experiments performed in the laboratory All strains of *B. crudilactis* (≧98% of the strains) ferment galactose, glucose, fructose, maltose, lactose, melibiose, sucrose, raffinose, and D-turanose. None ferment (≦2% of the strains) glycerol, erythritol, D-arabinose, L-arabinose, L-xylose, adonitol, β-methyl-xyloside, L-sorbose, rhamnose, dulcitol, inositol, mannitol, sorbitol, α-methyl-D-glucoside, N-acetyl-glucosamine, arbutin, trehalose, inulin, melezitose, starch, glygogen, xylitol, D-lyxose, D-tagatose, D-fucose, L-fucose, D-arabitol, L-arabitol, gluconate, 2-keto-gluconate, 5-keto-gluconate. All strains (≧98% of the strains) were positive for α-galactosidase, β-galactosidase, α-glucosidase, arginine arylamidase, proline arylamidase, phenylalanine arylamidase, leucine arylamidase, and histidine arylamidase. All were negative (≦2% of the strains) for urease, indole production, nitrate reduction, arginine dihydrolase, β-galactosidase-6-phosphate, α-arabinosidase, β-glucuronidase, β-N-acetylglucosaminidase, acide glutamique decarboxylase, α-fucosidase, acide pyroglutamique arylamidase, glutamyl arylamidase.

(f) G+C Content

The mean GC content (Tm method) of the FR62/b/3 strain of GC56 is 56% and of 9 strains in the group is 55.2% (SD=0.83).

(g) DNA-DNA Hybridization

DNA-DNA reassociation levels were between 4 and 36% with the type strains of all the *Bifidobacterium* species and of *Aeriscardovia aeriphila*, results shown in Table 4 below, and between 76 and 100% within the *Bifidobacterium* GC56 group (13 experiments). The DNA-DNA homology between *B. psychraerophilum* and the GC56 group reference strain (FR62/b/3) is equal to 31% (2 measurements) confirming that the GC56 group does not belong to that species (definition threshold of bacterial species upper or equal to 70%; Goebel and Stackebrandt, (1994), Appl Environ Microbiol, 60: 1614-1621; Rossello-Mora and Amann (2001), FEMS Microbiol Rev, 25: 39-67).

DNA-DNA reassociation levels were determined using the spectrophotometric method from renaturation rates described by De Ley et al. (*J. Biochem.* (1970) 12, 133-142), slightly modified in hybridization temperature (Gavini et al. *Ecology in Health and Disease* (2001) 13, 40-45). The determinations were performed at 67.3° C. ($T_m$-25° C. according to the G+C content of the strain FR62/b/3), using a spectrophotometer Cary 100 (Varian) related to a temperature controller (Peltier system, Varian).

TABLE 4

| Species | DNA Homology with FR62/b/3 (%) |
|---|---|
| *B. crudilactis* FR47/3, FR55/d/2, FR59/b/2, FR98/a/11 | 100 |
| *B. crudilactis* FR50/f/4 | 94 |
| *B. crudilactis* Brie/9 | 91 |
| *B. crudilactis* PicV/10 | 86 |
| *B. crudilactis* FR35/5 | 85 |
| *B. crudilactis* Reb/13 | 83 |
| *B. adolescentis* | 31 |
| *B. angulatum* | 36 |
| *B. animalis* | 31 |
| *B. asteroides* | 24 |
| *B. bifidum* | 21 |
| *B. boum* | 21 |
| *B. breve* | 21 |
| *B. catenulatum* | 34 |
| *B. choerinum* | 23 |
| *B. coryneforme* | 29 |
| *B. cuniculi* | 23 |
| *B. dentium* | 17 |
| *B. gallicum* | 19 |
| *B. gallinarum* | 6 |
| *B. indicum* | 21 |
| *B. longum* | 29 |

TABLE 4-continued

| Species | DNA Homology with FR62/b/3 (%) |
|---|---|
| B. magnum | 20 |
| B. merycicum | 16 |
| B. minimum | 22 |
| B. pseudocatenulatum | 26 |
| B. pseudolonum subsp. globosum | 16 |
| B. pseudolonum subsp. pseudolongum | 28 |
| B. psychraerophilum | 31 |
| B. pullorum | 21 |
| B. ruminantium | 15 |
| B. saeculare | 5 |
| B. scardovii | 35 |
| B. subtile | 13 |
| B. suis | 32 |
| B. thermacidophilum subsp. thermacidophilum | 21 |
| B. thermacidophilum subsp. porcinum | 26 |
| B. thermophilum | 4 |
| Aeriscardovia aeriphila | 28 |

Table 4 shows DNA-DNA reassociation of DNA from FR62/b/3 (GC56 group) with DNAs from type strains of the *Bifidobacterium* genus, including strains of *B. crudilactis* and of *Aeriscardovia aeriphila*.

*B. crudilactis* FR62/b/3 (GC56), *B. crudilactis* FR55/d/2, FR59/b/2, FR98/a/11, *B. crudilactis* FR50/f/4, *B. crudilactis* Brie/9, *B. crudilactis* PicV/10, *B. crudilactis* FR35/5 and *B. crudilactis* Reb/13 are all strains of *B. crudilactis* which have more than 80% DNA homology with *B. crudilactis* FR62/b/3.

(h) 16S rRNA Sequencing

The sequencing of the 16S rDNA (about 1400 bp) has been realized on 3 GC56 group representative strains (FR/62/b/3, FR/47/b/3, FR/59/b/2 strains) and was compared with other close *Bifidobacterium* sequences available on Genbank (FIG. 1). It appeared that this group presented 99.8% of similarities (3 differences) with *B. psychraerophilum* considering the FR62/b/3, FR/59/b/2 and the FR/47/b/3 strains.

A 16S rDNA sequence alignment of three GC56 strains with *B. psychraerophilum* was performed. Specific restriction enzyme areas were identified using AluI and TaqI (FIG. 2). Restriction fragment length polymorphism could be used to detect or to identify this group in a sample. No difference was observed with *B. psychraerophilum*. However, there is a low probability of finding *B. psychraerophilum* in these kind of samples.

(i) hsp60 Gene Partial Sequencing

FIG. 3 shows an hsp60 gene sequence alignment of several strains of the GC56 group (FR47/3, FR51/h/1, FR54/e/1, 59/b/2) with closely identified sequences found on Genbank (PubMed-BLAST). No difference was observed between the GC56 group strains while differences were observed with other bifidobacterial species. These differences were used for chosen specific PCR primers and a specific probe for real-time PCR (Table 1).

(j) Appearance

GC56 cells are Gram-positive, non-spore-forming bacilli, and irregularly shaped rods. The morphology of the FR62/b/3 strain is shown in FIG. 4.

*Bifidobacterium crudilactis* strain 62/b/3 has been deposited with the Collection Nationale de Cultures de Microorganismes (CNCM), Institut Pasteur, 28, Rue du Docteur Roux, F-75724, Paris Cedex 15, France, under deposit number CNCM I-3342 and deposited on Dec. 9, 2004.

The following *B. crudilactis* strains have been deposited with the Belgian Co-ordinated Collection of Micro-organisms (BCCM™), Laboratorium voor Moleculaire Biologie-Plasmidencollectie (LMBP) at the Universeit Gent, K. L. Ledeganckstraat 35, B-9000, Gent, Belgium:

| Strains | Deposit No. | Deposit Date |
|---|---|---|
| B. crudilactis FR50/f/4 | LMG P-25846 | Jun. 9, 2010 |
| B. crudilactis FR98/a/11 | LMG P-25847 | Jun. 9, 2010 |
| B. crudilactis FR59/b/2 | LMG P-25848 | Jun. 9, 2010 |
| B. crudilactis FR35/5 | LMG P-25849 | Jun. 9, 2010 |
| B. crudilactis Reb13 | LMG P-25850 | Jun. 9, 2010 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by CNCM and BCCM™ under the terms of the Budapest Treaty, and subject to an agreement between the Université de Liége and CNCM and the Université de Liége and BCCM™, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 C.F.R. §1.14 with particular reference to 8860G 638). Thereby, the deposited biological materials will be irrevocably and without restriction or condition released to the public upon the issuance of a patent.

The invention claimed is:

1. An isolated *Bifidobacterium crudilactis* strain comprising SEQ ID NO: 2, SEQ ID NO:3, or SEQ ID NO:4.

2. The isolated *Bifidobacterium crudilactis* strain of claim 1, wherein the strain comprises SEQ ID NO:3 and is FR62/b/3, deposited with the Collection Nationale de Cultures de Microorganismes, Institut Pasteur, under the accession number CNCM I-3342.

3. The isolated *Bifidobacterium crudilactis* strain of claim 1, wherein the strain comprises SEQ ID NO:4 and is FR59/b/2, deposited with the Belgian Coordinated Collection of Microorganisms (BCCM), under the accession number LMG P-25848.

4. A probiotic composition comprising a) one or more of the *Bifidobacterium crudalactis* strains of claim 1 and b) one or more excipients.

5. The probiotic composition of claim 4, wherein one or more of the excipients is selected from the group consisting of sugars, sugar alcohols, emulsifiers, thickeners, acidifiers, fruit juices, vitamins, minerals, reduced glutinous starch syrup, reduced glutinous maltose syrup, binding agents, fillers, tabletting lubricants, disintegrants, and acceptable wetting agents.

6. The probiotic composition of claim 4, wherein the composition is in the form of a tablet, a capsule, oral liquid preparation, food product, powder, granule, or lozenge.

7. The probiotic composition of claim 6, wherein the powder is a reconstitutable powder.

8. The probiotic composition of claim 7, wherein the reconstitutable powder is a lyophilized powder or spray-dried powder.

9. The Probiotic composition of claim 6, wherein the oral liquid preparation is reconstitutable suspension.

10. The probiotic composition of claim 4, wherein the composition is formulated as a conventional food product.

11. The probiotic composition of claim 10, wherein the food product is a dairy based product or fruit juice.

12. The probiotic composition of claim 11, wherein the dairy product is fermented milk, vegetable milk, soybean milk, butter, cheese, or yogurt.

13. A method of detecting an isolated *Bifidobacterium crudilactis* strain comprising amplifying a DNA sample by polymerase chain reaction (PCR), wherein SEQ ID NO:44 and SEQ ID NO:45 are primers for the PCR.

14. A method of detecting an isolated *Bifidobacterium crudilactis* strain comprising amplifying a DNA sample by polymerase chain reaction (PCR), wherein SEQ ID NO:43 is a probe for the PCR.

15. The method of claim 14, wherein the probe is labeled with a reporter dye.

16. The method of claim 15, wherein the reporter dye is a carboxyfluorescein.

17. An isolated *Bifidobacterium crudilactis* strain Reb13, deposited with the Belgian Coordinated Collection of Microorganisms (BCCM), under the accession number LMG P-25850, wherein the strain Reb13 has more than 80% DNA homology with the strain of claim 2.

18. An isolated *Bifidobacterium crudilactis* strain FR50/f/4, deposited with the Belgian Coordinated Collection of Microorganisms (BCCM), under the accession number LMG P-25846, wherein the strain FR50/f/4 has more than 80% DNA homology with the strain of claim 2.

19. An isolated *Bifidobacterium crudilactis* strain FR35/5, deposited with the Belgian Coordinated Collection of Microorganisms (BCCM), under the accession number LMG P-25849 wherein the strain FR35/5 has more than 80% DNA homology with the strain of claim 2.

20. An isolated *Bifidobacterium crudilactis* strain FR98/a/11, deposited with the Belgian Coordinated Collection of Microorganisms (BCCM), under the accession number LMG P-25847, wherein the strain FR98/a/11 has more than 80% DNA homology with the strain of claim 2.

* * * * *

UNITED STATES PATENT AND TRADEMARK OFFICE
CERTIFICATE OF CORRECTION

| | | |
|---|---|---|
| PATENT NO. | : 7,959,912 B2 | Page 1 of 1 |
| APPLICATION NO. | : 11/914434 | |
| DATED | : June 14, 2011 | |
| INVENTOR(S) | : Daube et al. | |

It is certified that error appears in the above-identified patent and that said Letters Patent is hereby corrected as shown below:

Col. 6, lines 45-46: "with a carboxvfluorescein (FAM)" should read --with a carboxyfluorescein (FAM)--

Col. 12, lines 47-48: "reference to 8860G 638)." should read --reference to 886 OG 638).--

Signed and Sealed this
Twenty-first Day of February, 2012

David J. Kappos
*Director of the United States Patent and Trademark Office*